United States Patent [19]

Luppi

[11] 4,073,622
[45] Feb. 14, 1978

[54] BLOOD OXYGENATOR WITH HEAT EXCHANGER

[76] Inventor: Libero Luppi, Via 5 Martiri, 13, Mirandola (Modena), Italy

[21] Appl. No.: 560,753

[22] Filed: Mar. 21, 1975

[30] Foreign Application Priority Data

Mar. 25, 1974 Italy .................. 12654/74

[51] Int. Cl.² ............................................. A61M 1/03
[52] U.S. Cl. ............................. 23/258.5 BH; 55/178; 128/DIG. 3; 210/177; 261/DIG. 28
[58] Field of Search ................. 23/258.5 B, 258.5 BH; 55/87, 178; 128/DIG. 3; 210/177, 201, 220, 320; 261/123, 156, DIG. 28

[56] References Cited

U.S. PATENT DOCUMENTS

| | | | |
|---|---|---|---|
| 2,934,067 | 4/1960 | Calvin | 23/258.5 BH |
| 3,256,883 | 6/1966 | DeWall | 23/258.5 BH |
| 3,291,568 | 12/1966 | Sautter | 23/258.5 BH |
| 3,468,631 | 9/1969 | Raible et al. | 23/258.5 BH |
| 3,764,271 | 10/1973 | Brumfield | 23/258.5 BH |
| 3,769,162 | 10/1973 | Brumfield | 128/DIG. 3 |
| 3,870,470 | 3/1975 | Yoshida et al. | 23/258.5 BH |
| 3,875,060 | 4/1975 | Noma | 210/201 X |

Primary Examiner—Charles N. Hart
Assistant Examiner—Robert H. Spitzer
Attorney, Agent, or Firm—Guido Modiano; Albert Josif

[57] ABSTRACT

A blood oxygenator with heat exchanger comprising an annular oxygenation chamber provided with a blood entry, an oxygen diffuser and a duct for the passage of the blood from the oxygenator chamber to a defoaming element. A heat exchanger is provided extending from an upper container housing the defoaming element to a second container located below the oxygenation chamber. In the oxygenation chamber the blood follows a labyrinth passage defined by radially disposed, longitudinally extending baffles uniformly distributed in the annular chamber.

11 Claims, 6 Drawing Figures

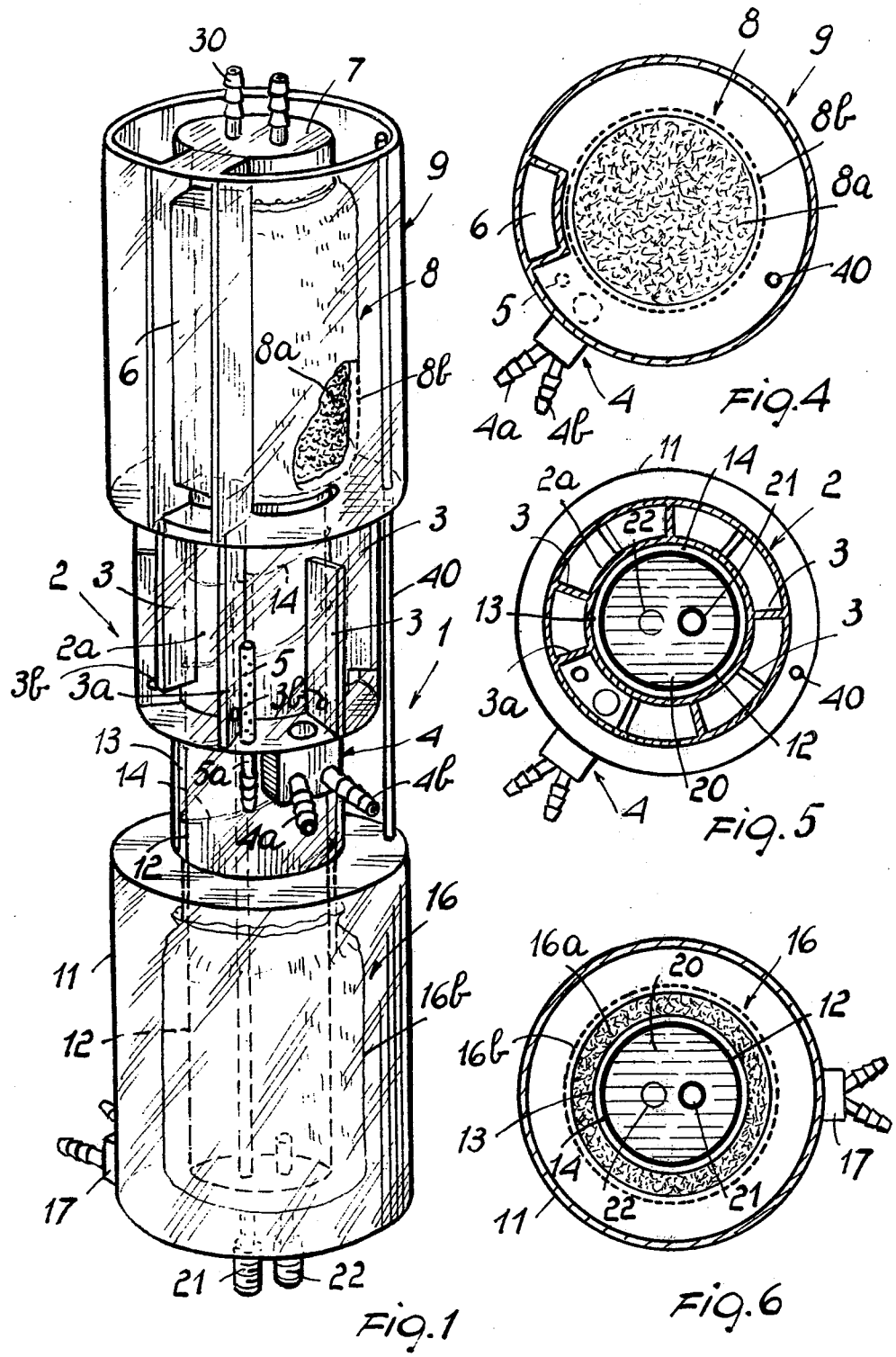

BLOOD OXYGENATOR WITH HEAT EXCHANGER

BACKGROUND OF THE INVENTION

This invention relates to a blood oxygenator with heat exchanger.

In certain surgical operations on the human body, extracorporal blood circulation must be set up for a certain period of time. For this purpose oxygenators are used which besides oxygenating the blood also allow the blood temperature to be raised or lowered as necessary.

While known oxygenators have given satisfactory results, they have presented certain disadvantages, the most felt of which consists of the fact that complete and perfect mixing between the blood and the oxygen is not always obtained, with the result that oxygenation is only partial.

A further disadvantage which often arises is the fact the oxygenators of known are considerably bulky, which creates utilisation and positioning problems. The object of the present invention is to eliminate the aforementioned disadvantages by providing a blood oxygenator with heat exchanger which ensures perfect and complete mixing between the oxygen and the blood, so providing total blood oxygenation.

A further object of the present invention is to provide an oxygenator of extremely compact form, this form being obtained by rationally and effectively distributing its component parts.

A further object of the present invention is to provide an oxygenator which allows the blood flow to be visually checked during its passage through the oxygenator.

A further object of the present invention is to provide an oxygenator which is easily constructed starting from elements commonly available commercially, which does not require any special manufacturing techniques and which is of very low cost, to the extent that it may be used as a "disposable" oxygenator, i.e. usable once only.

SUMMARY OF THE INVENTION

These and further objects, which will be more evident hereinafter, are attained by a blood oxygenator with heat exchanger, according to the invention, comprising an annular oxygenation chamber, a labyrinth passage in said annular chamber, a connector for venous blood entry and an oxygen diffuser at the beginning of said labyrinth passage, an ascending duct for the blood at the end of said labyrinth passage, an upper defoaming element on which said ascending duct opens, an upper container located above said annular chamber and containing said upper defoaming element, a lower container arranged below said annular chamber, a heat exchanger extending from the bottom of said upper container to the bottom of said lower container, an annular interspace defined between said heat exchanger and the inner wall of said annular chamber, said interspace connecting said upper container to said lower container for the passage of the defoaming blood, and an arterial connector located on the bottom of said lower container.

BRIEF DESCRIPTION OF THE DRAWINGS

Further characteristics and advantages will be more evident from the description of a preferred but not exclusive embodiment of an oxygenator with heat exchanger, illustrated by way of non-limiting example in the accompanying figures in which:

FIG. 1 is a perspective view of the oxygenator;
FIG. 4 is a section on the line IV—IV of FIG. 3;
FIG. 5 is a section on the line V—V of FIG. 3;
and
FIG. 6 is a section on the line VI—VI of FIG. 3.

DESCRIPTION OF A PREFERRED EMBODIMENT

Figures 2, 3:
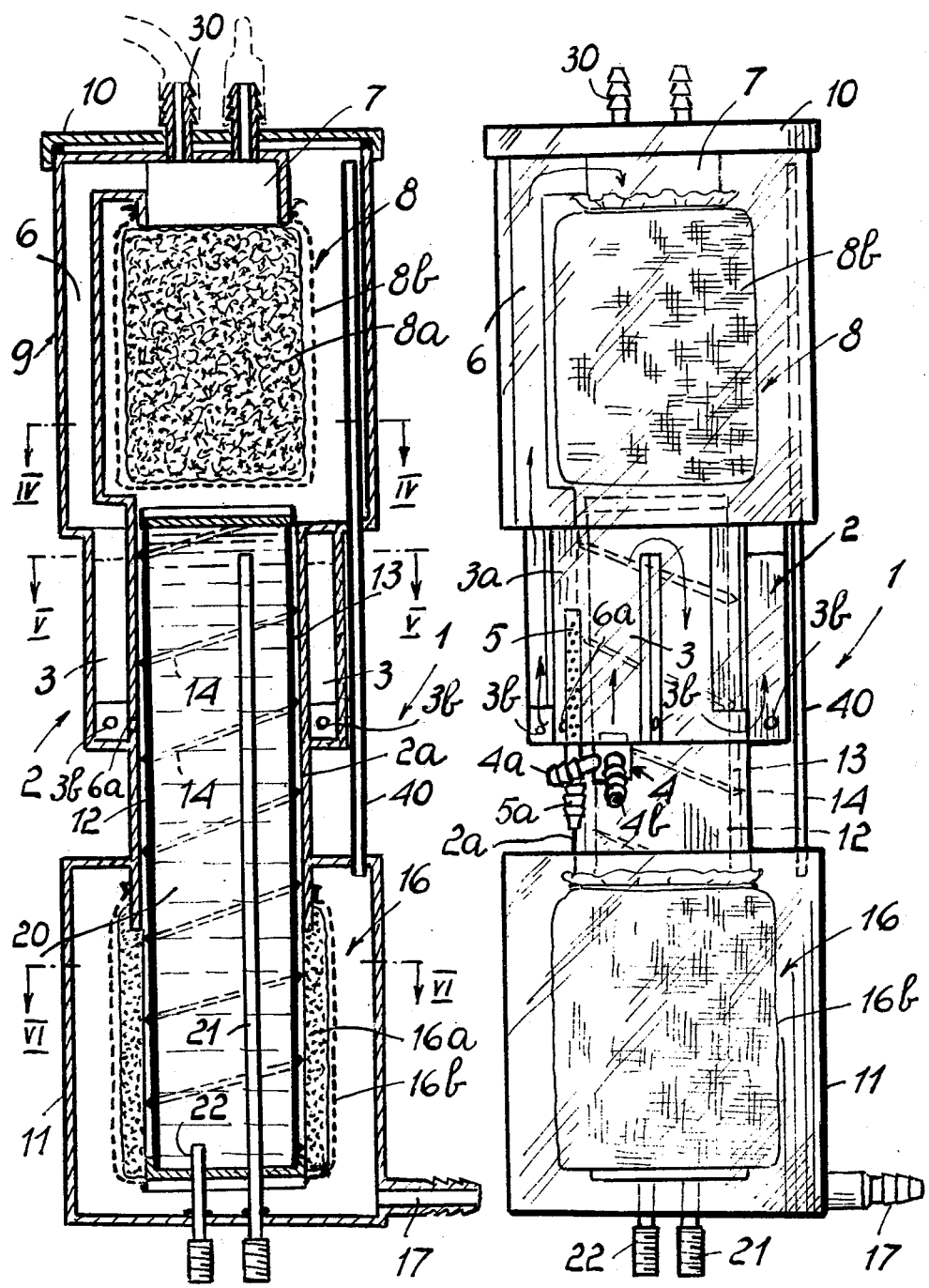
FIG. 2 is an elevational view of the oxygenator.
FIG. 3 is a longitudinal section through the oxygenator on an axial plane.

With reference to said figures, the oxygenator 1 comprises an annular oxygenation chamber 2 which extends upwards through a certain distance and is located in an intermediate position in the oxygenator according to the invention.

It will be appreciated that the annular chamber 2 is formed of concentric cylindrical wall portions.

Inside said annular chamber 2 there are radially directed baffles 3 extending longitudinally and distributed uniformly inside the annular chamber 2. Said baffles 3 are interrupted alternately at their upper and lower ends so as to define a labyrinth passage within the annular chamber 2, this labyrinth passage being of serpentine development. There are thus ascending baffles 3 with the interruption at their upper end alternating with descending baffles 3 with the interruption at their lower end.

To avoid stagnant blood zones forming between two ascending baffles, a hole 3b of small diameter (1-2 mm) is formed at the base of the ascending baffles to connect together the various compartments, so allowing a minimum but constant exchange of blood. In fact, should stagnant zones form between ascending baffles, the said stagnant zones would receive an excessive oxygen flow, leading to high haemolysis.

A connector 4 is located at the beginning of said labyrinth passage for the entry of venous blood into the annular chamber 2, this connector being preferably of Y shape so as to comprise a nozzle 4a and a nozzle 4b for connection to the venous blood feed tubes. At the beginning of the labyrinth passage there is an oxygen diffuser 5 which extends over a certain distance inside the annular chamber 2, and comprises externally a connector 5a for connection to an oxygen supply.

An ascending duct 6 for the blood extends from the annular chamber 2 at the end of said labyrinth passage. The zone from which the ascending duct 6 extends is adjacent to the zone of commencement of the labyrinth passage, but the two zones are separated by a dividing baffle 3a with no interruptions, so that there is no direct communication between the ending zone communicating with of the ascending duct 6 and the zone of commencement of the labyrinth passage, such communication existing only through the labyrinth passage itself. The ascending duct 6 extends vertically and opens into a collection zone 7 lying above, and in lower communication, with an upper defoaming element 8. The upper defoaming element 8 consists of a cylinder 8a of non-toxic material covered with a defoaming substance contained in a bag 8b constructed of synthetic non-toxic material, its mouth being fixed to the lower mouth of said collection zone 7, for example by tying. The bag 8b forms a filter element permeable to the blood.

The defoaming element 8 is located axially in an upper cylindrical container 9, which also encloses said ascending duct 6 and the collection zone 7. Upperly the container 9 is closed by a cover 10 comprising a vent which allows the gas which develops during use of the oxygenator to pass to the atmosphere.

The oxygenator also comprises a lower cylindrical container 11 located below said annular chamber 2. It will be appreciated that the upper container 9 and the lower container 11 are connected by a tubular member 2a, a portion of the cylindrical wall of said tubular member 2a coinciding with the inner cylindrical wall portion of the annular chamber 2.

A cylindrical heat exchanger 12 extends downwards from the bottom of the upper container 9 and reaches the bottom of the lower container 11.

A duct in the form of an annular interspace 13 is defined between said heat exchanger 12 and the inner wall 2a of said annular chamber 2 and allows the defoamed blood to pass from the upper defoaming element 8 to the lower container 11.

A helically extending rib 14 is provided in the interspace 13 on the outer surface of the heat exchanger 12, its purpose being to increase the length of the path which the defoamed blood has to take in passing from the upper container 9 to the lower container 11. By increasing the time of contact between the defoamed blood and the heat exchanger in this manner, heat transfer between the blood and exchanger is facilitated, so allowing the defoamed blood to reach the desired temperature. Furthermore, the width of the interspace 13 is extremely small so that in passing from the upper container 9 to the lower container 11, the movement of the blood is laminar in practice, so avoiding turbulence and further facilitating heat transfer.

That part of the heat exchanger 12 disposed inside the lower container 11 is embraced by a lower defoaming element 16 consisting of a defoaming non-toxic material 16a in the form of a sleeve and contained in a non-toxic sheath 16b of filtering effect and permeable to blood. The purpose of the lower defoaming element 16 is to completely eliminate any gas particles which may have remained in the blood or have developed during the heating stage in spite of its passage through the upper defoaming element 8.

The blood which leaves the sheath 16b is collected in the lower container 11, on the bottom of which is an arterial collector 17 of Y shape which enables the oxygenated and filtered blood to be reintroduced into the patient's blood cycle.

The heat exchanger 12 consists of a cylinder of heat conducting material which is internally hollow and filled with a sponge-like packing element indicated overall by 20. An outlet tube 21 for the thermal fluid extends inside the exchanger 12 and reaches close to the top of the heat exchanger 12. A feed tube 22 extends from the bottom of the heat exchanger 12. When the thermal fluid, generally water, is fed at a predetermined temperature through the feed tube 22, the water passes through the internal body of the exchanger 12, transfers its heat and leaves through the outlet tube 21.

The oxygenator 1 also comprises inlet connectors 30 which enable a part of the blood to be fed directly into the collection zone 7 without previously passing it into the oxygenation chamber 2.

At the base of the ending zone of the labyrinth passage the wall 2a of the annular chamber 2 there is a radial hole 6a which connects the chamber 2 directly to the interspace 13. The purpose of the hole 6a is to allow the blood to be completely emptied from the annular chamber 2 after the patient has been treated. In this way the patient can receive the maximum possible quantity of blood, some of which would otherwise be lost. Any foam which passes through the hole 6a is eliminated by said lower defoaming element 16.

The operation of the oxygenator according to the invention is as follows. The venous blood to be purified is fed through the venous connector 4 to the beginning of the labyrinth passage in the annular oxygenation chamber 2. The blood fed into the chamber 2 mixes with the oxygen supplied from the diffuser 5, and is then thrust into the annular chamber 2 following the labyrinth passage defined by the baffles 3.

As stated, the labyrinth passage is formed by the baffles 3 which are interrupted alternatively at their upper end and lower end, and this leads to intimate mixing of the blood and oxygen during passage. After the blood has passed through the entire oxygenation chamber 2, which it does in practice in the form of a foam, it flows through the ascending duct 6 and enters the collection zone 7, then arriving in the upper defoaming element, the purpose of which is to eliminate bubbles and release the gas particles which have not dissolved in the blood. The blood which has been oxygenated and separated from the excess gas collects on the bottom of the upper container 9 and flows from it by gravity through the annular interspace 13, lapping the walls of the heat exchanger 12. The blood may be heated by this means to the required temperature. As stated, during this stage the blood is under practically laminar flow and moves helically about the heat exchanger 12.

The oxygenated blood continues to lap the heat exchanger 12 and arrives in the lower container 11 after undergoing a further defoaming stage. In this respect, that part of the heat exchanger 12 situated in the container 11 is surrounded by a lower defoaming element. This ensures completely that the blood returned to the patient's blood cycle is free of gas traces. The lower container 11 is connected to the upper container 9 by a tube 40 which extends vertically and has its outlet close to the cover 10 of the upper container 9. The purpose of the tube 40 is to vent gas and air from the lower container 11.

The device according to the invention is preferably constructed of optically transparent plastics materials, and this enables the progress of oxygenation of the blood to be visually followed, and allows prompt action by the operator if necessary.

From the description it can be seen that the oxygenator according to the invention attains all the proposed objects, and in particular, the relative arrangement of its component elements, which are disposed essentially vertically, is very functional and considerably reduces overall dimensions, and furthermore the inclusion of two defoaming elements, i.e. an upper and a lower defoaming element, completely guarantee that the blood returned to the patient's blood cycle is free of gas traces.

The invention so conceived is susceptible to numerous modifications all of which fall within the scope of the inventive idea.

Furthermore all details may be replaced by other technically equivalent elements.

In practice, although the best results are obtained by using non-toxic plastics materials, the materials and dimensions may be chosen according to requirements.

I claim:

1. A blood oxygenator comprising an upper container and a lower container arranged at a distance therefrom, a tubular member arranged between and connecting said upper and lower containers, concentric cylindrical wall portions defining an annular chamber having an axial extension between said upper and lower containers and surrounding said tubular member, means defining a labyrinth passage in said annular chamber, said labyrinth passage having a start and an opposite end thereof and defining means directing the blood in said labyrinth passage in a direction parallel to said concentric cylindrical wall portions thereof, a heat exchanger unit extending from said upper container through the interior of said tubular member into said lower container, inlet and outlet means for the heating fluid into the heat exchanger, first defoaming means arranged in said upper container and second defoaming means arranged in said lower container, first duct means on one side of said first defoaming means and connecting said opposite end of said labyrinth passage with said upper container, second duct means on the other side of said first defoaming means and extending through the interior of said tubular member around said heat exchanger unit and connecting said upper container with said lower container, first connector means defining a blood inlet at the start of said labyrinth passage for the venous bloody entry, second connector means defining a blood exit at the bottom of said lower container for the arterial blood exit and an oxygen diffuser at said beginning of the labyrinth passage said second duct means ending on one side of said second defoaming means and said second connector means opening with one end thereof at the other side of said second defoaming means and ending with the other end thereof outside said lower lower container, thereby to allow oxygenated blood coming from said labyrinth passage to flow from said upper container past said heat exchanger unit-into said lower container and to undergo a first defoaming action in said first container and after heating action by said heating unit a second defoaming action in said second container.

2. A blood oxygenator according to claim 1, wherein said labyrinth passage defining means comprise a plurality of circumferentially uniformly distributed baffles of vertical extension alternatively interrupted at their opposite ends to define a serpentine path for the blood within said annular chamber.

3. An oxygenator according to claim 2, wherein some of said baffles have at least one through hole allowing restricted blood passage from one side of the baffle to the other in order to avoid stagnant blood zones in the labyrinth passage.

4. A blood oxygenator according to claim 1, wherein one of the concentric wall portions of said annular chamber coincides with a wall portion of said tubular member and wherein said one wall portion has a through hole near the bottom of said annular chamber providing restricted blood passage from said annular chamber into said second duct means and therefrom into said lower container.

5. An oxygenator according to claim 1, wherein said upper container has means defining a substantially cylindrical collection zone at the upper portion thereof and wherein said first duct means open into said collection zone, and wherein said collection zone has a lower cylindrical opening in communication with said first defoaming means.

6. An oxygenator according to claim 5, wherein said first defoaming means comprises a blood permeable bag of synthetic non-toxic material surrounding said lower cylindrical opening and a substantially cylindrical defoaming element of non-toxic material covered with a defoaming substance and contained in said bag.

7. An oxygenator as claimed in claim 1, wherein said second duct means is in the form of an annular interspace surrounding said heat exchanger unit and has helically extending rib means causing the blood to flow along a helical path during its passage from said upper container to said lower defoaming means, said annular interspace being of substantially reduced radial width for obtaining a laminar flow of the blood passing therethrough.

8. An oxygenator as claimed in claim 1, wherein said heat exchanger unit comprises a hollow cylinder of heat-conducting material, a sponge-like packing material contained in said hollow cylinder, an outlet duct for the heat transfer fluid and having its mouth arranged close to a top of said heat exchanger unit, and a feed tube for said heat transfer fluid and having its mouth arranged close to a bottom of said heat exchanger unit.

9. An oxygenator according to claim 1, further comprising a cover for closing said upper container, said cover having a vent.

10. An oxygenator according to claim 1, wherein said upper container has means defining a substantially cylindrical collection zone and wherein the oxygenator further comprising at least an additional connector for feeding blood directly into said collection zone of said upper container.

11. An oxigenator according to claim 1, wherein said second defoaming means comprise a non-toxic sheath permeable to blood and a sleeve-like element of defoaming material arranged therein.

* * * * *